United States Patent [19]

Simcox et al.

[11] Patent Number: 5,300,432
[45] Date of Patent: Apr. 5, 1994

[54] OCTANUCLEOTIDE RESTRICTION ENDONUCLEASE, SRF I, AND METHOD FOR PRODUCING THE SAME

[75] Inventors: Timothy G. Simcox; Mary E. Simcox, both of Del Mar, Calif.

[73] Assignee: Stratagene, La Jolla, Calif.

[21] Appl. No.: 65,078

[22] Filed: May 20, 1993

Related U.S. Application Data

[63] Continuation of Ser. No. 778,772, Oct. 18, 1991.

[51] Int. Cl.$^5$ ............................................. C12N 9/22
[52] U.S. Cl. ........................................ 435/199; 435/886
[58] Field of Search ................................ 435/199, 886

[56] References Cited

PUBLICATIONS

Simcox, T. G., et al. (1991) 109, 121–123.
Kessler, C. et al, (1990) Gene 92, 1, 241, 245.
Kotani et al, "Sse8387I, a New Type-II Restriction Endonuclease That Recognizes the Octanucleotide Sequence 5'-CCTGCAGG-3'," *Nucleic Acids Res.*, 18:5637–5640 (1990).
Nelson et al, "FseI, a New Type II Restriction Endonuclease That Recognizes the Octanucleotide Sequence 5' GGCCGGCC 3', " *Nucleic Acids Res.*, 18:2061–2064 (1990).
Roberts, "Restriction Enzymes and Their Isoschizomers," *Nucleic Acids Res.*, 18:2331–2365 (1990).
Roberts et al, "Restriction Enzymes and Their Isoschizomers," *Nucleic Acids Res.*, 20:2167–2180 (1992).
Tauts et al, "SgrAI, a Novel Class-II Restriction Endonuclease from Streptomyces Griseus Recognizing the Octanucleotide Sequence 5'-CR/CCGGYA-3', " *Nucleic Acids Res.*, 18:3087 (1990).

*Primary Examiner*—Charles L. Patterson, Jr.
*Attorney, Agent, or Firm*—Albert P. Halluin; Scott R. Bortner

[57] ABSTRACT

This invention provides restriction endonuclease, Srf I, capable of recognizing the eight nucleotide base palindromic sequence shown below on a double-stranded DNA molecule and cleaving the DNA chain at the asterisk-marked position resulting in blunt ends

5' GCCC*GGGC 3'
3' CGGG*CCCG 5'

(wherein C and G respectively represent cytosine and guanine). The restriction endonuclease is produced by culturing Streptomyces rf in a culture medium and recovering it from the culture.

7 Claims, 3 Drawing Sheets

```
27205      5'-CAGCG CCATTATGAG CAAGGAAATT CCCACGCCCT    27239
           ACATGTGGAG TTACCAGCCA CAAATGGGAC TTGCGGCTGG    27279
           AGCTGCCCAA GACTACTCAA CCCGAATAAA CTACATGAGC    27319
           GCGGGACCCC ACATGATATC CCGGGTCAAC GGAATCCGCG    27359
           CCCACCGAAA CCGAATTCTC CTCGAACAGG CGGCTATTAC    27399
           CACCACACCT CGTAATAACC TTAATCCCCG TAGTTGGCCC    27439
           GCTGCCCTGG TGTACCAGGA AAGTCCCGCT CCCACCACTG    27479
           TGGTACTTCC CAGAGACGCC CAGGCCGAGG TTCAGATGAC    27519
           TAACTCAGGG GCGCAGCTTG CGGGCGGCTT TCGTCACAGG    27559
           GTGCGGTCGC CCGGGCAGGG TATAACTCAC CTGAAAATCA    27599
           GAGGGCGAGG TATTCAGCTC AACGACGAGT CGGTGAGCTC    27639
           CTCTCTTGGT CTCCGTCCGG ACGGGACATT TCAGATCGGC    27679
           GGCGCTGGCC GCTCTTCATT TACGCCCCGT CAGGCGATCC    27719
           TAACTCTGCA GACCTCGTCC TCGGAGCCGC GCTCCGGAGG    27759
           CATTGGAACT CTACAATTTA TTGAGGAGTT CGTGCCTTCG    27799
           GTTTACTTCA ACCCCTTTTC TGGACCTCCC GGCCACTACC    27839
           CGGACCAGTT TATTCCCAAC TTTGACGCGG TGAAAGACTC    27879
           GGCGGACGGC TACGACTGAA TGACCAGTGG AG-3'          27911
```

OCTANUCLEOTIDE RESTRICTION ENDONUCLEASE, SRF I, AND METHOD FOR PRODUCING THE SAME

CROSS REFERENCE TO RELATED APPLICATION

This application is a continuation of pending U.S. application Ser. No. 07/778,772 filed Oct. 18, 1991, the disclosures of which are hereby incorporated by reference.

TECHNICAL FIELD

This invention provides restriction endonuclease, Srf I, capable of recognizing an eight nucleotide base palindromic sequence on a double-stranded DNA molecule and cleaving the DNA chain to result in blunt ends. The restriction endonuclease is produced by culturing Streptomyces rf in a culture medium and recovering it from the culture.

BACKGROUND

Restriction endonucleases are capable of recognizing a specific sequence of bases of a deoxyribonucleic acid (DNA) molecule and of enzymatically cleaving in a process termed restriction the double-stranded DNA chain at specific sites. Different restriction endonucleases have an affinity for different recognition sequences. When they are purified away from other contaminating bacterial components, restriction endonucleases can be used in the laboratory to cut DNA molecules into specific fragments. This property enables DNA molecules to be uniquely identified and to be fractionated into their constituent genes. Restriction endonucleases, thus, allow the researcher to manipulate the DNA molecule and analyze the resulting construction.

Bacteria usually possess a limited number of restriction endonucleases per species. The endonucleases are named according to the bacteria from which they are derived. For example, the species *Proteus vulgaris* contains two known restriction endonucleases, named Pvu I and Pvu II. These restriction enzymes recognize and cleave the sequences CGATCG, and CAGCTG respectively. *E. coli* RY13, on the other hand synthesizes only one enzyme, Eco RI which recognizes the sequence GAATTC.

More than 1000 class-II restriction endonucleases have been identified. See, Kessler et al., *Gene*, 47:1–153 (1986) and Roberts, *Nuc. Acids Res.*, 17:347–387 (1989) and Kessler et al., *Gene*, 92:1–248 (1990). The majority of these enzymes recognize four or six basepair palindromic sequences. Thus far, only eight restriction endonucleases with octanucleotide recognition sequences have been found: Asc I (5'-GG/CGCGCC-3', New England Biolabs, Beverly, MA); Fse I (5'-GGCCGG/CC-3', Nelson et al, *Nucl. Acids Res.*, 18:2061–2064 (1990); Not I (5'-GC/GGCCGC-3', Qiang et al., *Nucl. Acids Res.*, 12:4507–4515 (1984); pac I (5'-TTAAT/TAA-3', Polisson et al., unpublished observations; Sfi I (5'-GGCCNNNN/NGGCC-3', where N is either A, C, G or T, Qiang et al., supra; Sgr AI (5'-CR/CCGGYA-3', where R is either A or G and Y is either C or T, Tantz et al., *Nucl. Acids Res.*, 18:3087–3089 (1990); Sse 8287 I (5'-CCTGCA/GG-3', Kotani et al., *Nucl Acids Res.*, 8:5637–5640 (1990); and Swa I (5'-ATTTAAAT-3', Boehringer Mannheim Biochemicals, Indianapolis, IN). Restriction enzymes having these specificities are especially useful for mammalian genome analysis. The purification and characterization of a novel octanucleotide restriction endonuclease, designated Srf I, is the subject of this invention.

BRIEF DESCRIPTION OF THE INVENTION

The present invention provides a new restriction endonuclease with specificity for an octanucleotide palindromic sequence, the cleavage of which results in DNA having blunt ends. A preferred method for producing purified Srf I restriction endonuclease from a culture of Streptomyces rd (ATCC Budapest Treaty Deposit Accession Number 55215) is also provided. The Streptomyces rf strain was deposited with the American Type Culture Collection (ATCC Bethesda, MD) on August 1, 1991 by the depositor (Stratagene, La Jolla, CA) and has been assigned a deposit accession number that is available from the ATCC.

The invention, thus, relates to a new restriction endonuclease, Srf I, having the following properties:

(a) Substrate specificity—The endonuclease recognizes the palindrmic nucleotide base sequence as shown below for each respective strand on a double-stranded DNA molecule and cleaves the DNA at the asterisk-marked position to result in DNA having blunt ends

5' GCCC*GGGC 3'
3' CGGG*CCCG 5'

(wherein C and G respectively represent the nucleotides, cytosine and guanine);

(b) Optimal pH range—7.0 to 8.0; preferred pH is 7.6;

(c) Stable pH range—6.0 to 8.5;

(d) Optimal temperature—37 degrees Celsius (37° C.);

(e) Optimal salt concentration range—50 to 100 mM potassium acetate is preferred; the endonuclease activity is also maintained in sodium chloride concentrations up to 50 mM, but is retarded at higher levels and completely inhibited in 150 mM sodium chloride;

(f) Optimal magnesium acetate concentration range—the endonuclease activity is maximal in 5 to 10 mM of magnesium acetate; the activity is also maintained in 10 mM magnesium chloride;

(g) Optimal buffer concentration—25 mM Tris-acetate; the endonuclease activity is also maintained in a Tris-HCl buffer ranging in concentration from 10 to 25 mM.

This invention also relates to the method for producing the novel restriction endonuclease, Srf I, which comprises growing a Streptomyces rf culture corresponding to that deposited under ATCC Accession Number 55215 and capable of producing Srf I in a culture medium, and recovering the Srf I thus formed from the culture.

BRIEF DESCRIPTION OF THE DRAWINGS

FIG. 2 illustrates the cleavage of PCR amplified Adenovirus-2 regions containing putative recognition sequences. Lanes: 1 and 9, Hae III digest of PhiX174 as a size marker; 2 and 10, Hinf I digest of PhiX174 as a size marker; 3, PCR fragment A (Ad-2 nucleotide (nt) 27650 to nt 27911); 4, Fragment A maintained with Srf I; 5, Fragment B (Ad-2 nt 27585 to nt 27727); 6, Fragment B maintained with Srf I; 7, Fragment C (Ad-2 nt 27205 to nt 27627); 8, Fragment C maintained with Srf I. Restriction endonuclease activity was assayed by maintenance of each PCR fragment in 1X Universal Buffer (Stratagene) (10X Universal Buffer: 1M KAc, 250 mM Tris-Acetate, pH 2.6, 100 mM MgAc, 5 mM beta-mercaptoethanol, and 100 µg/ml bovine serum albumin (BSA)) with 0 or 1 U of Srf I at 37° C. for 3 hours. Restriction fragments were analyzed by electrophoresis in a 10% polyacrylamide gel prepared in TBE buffer.

FIG. 3 illustrates the determination of the Srf I cleavage specificity by a primed synthesis reaction performed as described in Example 2b. Lanes: G, A, T and C, the sequencing ladders through the Srf I recognition sequence; 5, Srf I-cleaved extension reaction; 6, Klenow fill-in reaction of Srf I-cleaved extension reaction; 7, Srf I-cleaved extension reaction plus "C" dideoxy sequencing reaction; 8, Klenow fill-in reaction of Srf I-cleaved extension reaction plus "C" dideoxy sequencing reaction. Standard dideoxy sequencing reactions as described by Sanger et al., *Proc. Natl. Acad. Sci., USA*, 74:5463–5467 (1977), were performed using a pBluescript II SK +derivative (pSMSrf I), with an insert containing a Srf I cleavage site as template, the M13(−20) primer and T7 DNA polymerase. Four µl of each sequencing reaction were loaded onto an 8% denaturing polyacrylamide gel. Srf I substrate for cleavage reactions was generated by extension of the M13(−20) primer with the four deoxynucleotides including $\alpha^{35}$-S-dATP T7 DNA polymerase on plasmid, pSMSrf I, template. After splitting the extension reactions, cleavage reactions were conducted using 6 U of Srf I for 15 minutes at 37° C. Four µl of each cleavage reaction +/− Klenow fill-in (Klenow fill-in kit, Stratagene), were loaded per lane. Two µl of cleavage reaction +/− Klenow fill-in were admixed with 2 µl "C" sequencing reaction to illustrate gel shift of cleavage products.

DETAILED DESCRIPTION OF THE INVENTION

Any species of Streptomyces that is capable of producing Srf I can be used for the purpose of this invention. A typical example, Streptomyces rf has been deposited at the American Type Culture Collection (ATCC), Rockville, MD under the Accession Number 55215. These can be grown in a jar fermentor by the usual method, and the grown microbial cells separated from the culture liquid by centrifugation.

Restriction endonuclease Srf I has the following properties:

(a) Substrate specificity—The endonuclease recognizes the palindromic nucleotide base sequence as shown below for each respective strand on a double-stranded DNA molecule and cleaves the DNA at the asterisk-marked position to result in DN having blunt ends

5' GCCC*GGGC 3'
3' CGGG*CCCG 5'

(wherein C and G respectively represent the nucleotides, cytosine and guanine);

(b) Optimal pH range—7.0 to 8.0; preferred pH is 7.6;

(c) Stable pH range—6.0 to 8.5;

(d) Optimal temperature—37 degrees Celsius (37° C.);

(e) Optimal salt concentration range—50 to 100 mM potassium acetate is preferred; the endonuclease activity is also maintained in sodium chloride concentrations up to 50 mM, but is retarded at higher levels and completely inhibited in 150 mM sodium chloride;

(f) Optimal magnesium acetate concentration range—the endonuclease activity is maximal in 5 to 10 mM of magnesium acetate; the activity is also maintained in 10 mM magnesium chloride;

(g) Optimal buffer concentration—25 mM Tris-acetate; the endonuclease activity is also maintained in a Tris-HCl buffer ranging in concentration from 10 to 25 mM.

Srf I can be extracted and purified using known techniques commonly employed for restriction enzymes. The cultured cells are collected from their growth medium and dispersed in a suitable buffer. Subsequently, the cells are disrupted, typically by the application of one or a combination of shear force, osmoic pressure, ultrasound and the like, to permit extraction of the endonuclease by the buffer solution. After removal of cellular debris, such as by centrifugation, the supernatant is subjected to the various methods known for protein fractionation, such as gel filtration, gel chromatography, ultrafiltration, electrophoretic mobility, ion exchange, dialysis, and the like, to separate and recover a protein with the above described characteristics from the other proteins present.

For instance, it is well known in the art that affinity chromatography on heparin-sepharose can be used to reproducibly isolate proteins from complex biological sources. Proteins in a solution are applied to a column containing an affinity matrix and subsequently eluted therefrom according to the salt ion concentration of a buffer passing through the column. Eluate fractions are collected and those containing the above-described restriction enzymes are recovered. After dialysis to remove excess salt, the partially purified Srf I isolate can be further purified, typically by a series of further chromatographic separations. Particularly useful are those utilizing Blue sepharose, Mono S FPLC and Mono Q FPLC, all obtainable from Pharmacia, Piscataway, NJ, and phosphocellulose available from Whatman Biosystems Limited, Maidstone, Kent, England.

The isolated Srf I is typically admixed in an aqueous solution, which can contain one or more of a pH buffering agent, reducing agent, ion-chelator, surfactant, stabilizing protein such as bovine serum albumin (BSA), and stabilizer such as glycerol. Preferred aqueous compositions contain Srf I at a concentration of at least 1 unit/μl more preferably at a concentration of at least 4 units/μl and most preferably at least 10 units/μl. Of course, concentrations at least as high as 15 units/μl, 20 units/μl and 30 units/μl are also contemplated.

EXAMPLES

The following examples are given to illustrate embodiments of the present invention as it is presently preferred in practice. It will be understood that these examples are illustrative of the invention and are not to be considered as limiting.

1. Preparation of Srf I Restriction Endonuclease a. Preparation of Crude Streptomyces Cell Extracts Eight Streptomyces bacterial strains were screened for endonuclease activities. All eight strains were separately maintained at 30 degrees Celsius (30° C.) in Streptomyces media, which contained 1% peptone, 0.1% yeast extract, 1% glucose, 10 millimolar (mM) Tris-HCl (Tris[hydroxymethyl] aminomethane-hydrochloride) at pH 7.5, until the cells reached the late logarithmic phase of growth. Twenty grams of cells were obtained from each Streptomyces culture by centrifugation at 10,000 rpm for ten minutes in a Beckman JA20 centrifuge to form a cell pellet. Each pellet was separately resuspended in Buffer A (10 mM potassium phosphate ($KPO_4$), 10 mM beta-mercaptoethanol and 1 mM EDTA [ethylene-diaminetetraacetic acid]) to form a cell suspension before passing through a Mouton-Gaulin press at 12,000 psi. The resultant slurries were maintained separately at less than 4° C. but above freezing during disruption and throughout further enzyme purification. For each strain screened, the salt concentration was increased to 0.3 M potassium chloride (KCl) and the suspension was then centrifuged for 1 hour at 12,000 rpm (Beckman) to pellet the cellular debris.

The resulting supernate containing the extracted (isolated) restriction endonucleases was diluted at a 1:3 ratio with Buffer A and applied onto a heparin sepharose column (1.5 cm × 7 cm) (Pharmacia, Piscataway, NJ) previously equilibrated with Buffer A containing 0.1 M KCl. A KCl gradient (0.1 M to 0.8 M) was used to elute Srf I activity immobilized on the column. One milliliter (ml) fractions were collected and DNA cleavage activity in the collected fractions was measured in an endonuclease assay as described below on the following DNA substrates: Phage Lambda (dam., dcm.), Adenovirus-2, pBR322, PhiX174, T7, SV40 and T5.

b. Endonuclease Activity of Crude Streptomyces Extracts

Endonuclease activity was measured by admixture of 8, 4, 2 and 1 microliter(s) (μl) of each of the column fractions for each of the eight extracted Streptomyces strains prepared in Example 1a with 0.25 microgram (μg) of each of the following DNA substrates: Phage Lambda (dam., dcm.) (Stratagene); Adenovirus-2 (Ad-2) (Bethesda Research Laboratories, Gaithersburg, MD); pBR322 as described by Bolivar et al., *Gene*, 2:95-116 (1977) (Stratagene); PhiX174 (Stratagene), T7 (Sigma Chemical, St. Louis, MO); SV40 (Sigma); and T5 (Sigma). The phage lambda DNA template was isolated from bacteriophage lambda CI859 ind/Sam 7 grown in *E. coli* strain JM110 (dam, dcm). The admixtures were diluted to 1X Universal Buffer (Stratagene) which was diluted from a 10X Universal Buffer stock solution of 250 mM Tris-acetate at pH 7.6, 1 M potassium acetate, 100 mM magnesium acetate, 5 mM beta-mercaptoethanol and 100 μg/ml of bovine serum albumin (BSA). The separate Streptomyces crude cell extracts-DNA substrate admixtures were maintained for 30 minutes at 37° C. to allow endonucleolytic cleavage activity to occur.

After the maintenance period, the substrate DNAs were separately admixed with gel-loading buffer and electrophoresed on a 1% agarose gel following procedures well known to one skilled in the art (Maniatis et al., *Molecular Biology: A Laboratory Manual*, eds., Cold Spring Harbor Laboratory, (1989)) in order to visualize the restriction endonuclease cleavage products. Crude extracts from one strain of Streptomyces exhibited endonuclease activity on Adenovirus-2 DNA but not on any of the other DNA substrates evaluated. A restriction endonuclease with this limited cleavage specificity has not been described before this present invention. The Adenovirus-2 DNA was cleaved only in one place resulting in two fragments of 27,571 and 8,366 base pairs in length. The Streptomyces strain, from which the Adenovirus-2 DNA-cleaving restriction endonuclease was isolated, was then selected for further purification and characterization of the novel restriction endonuclease. The selected strain, designated Streptomyces rf has been deposited in accordance with the Budapest Treaty and has been assigned ATCC Accession Number 55215.

c. Purification of the Novel Streptomyces Restriction Endonuclease, Srf I

To purify sufficient quantities of the novel restriction endonuclease, designated Srf I, described above for subsequent characterization assays, 600 grams of cells were harvested from a late log phase culture of the selected Streptomyces rf by centrifugation as described in Example 1a. The pelleted cells were then resuspended in Buffer B (10 mM Tris-HCl at pH 7.8, 10 mM beta-mercaptoethanol, 5 mM EDTA, 10 mM ammonium sulfate, 1% glycerol, 0.1% Triton X-100). After several passes through a Mouton-Gaulin press at 12,000 psi at non-freezing temperatures less than 4° C., the resultant cell slurry was brought to 0.3 M KCl and centrifuged at 12,000 rpm in a Beckman centrifuge equipped with a JA14 rotor for 2 hours to pellet cellular debris. The isolated endonuclease (supernate) was recovered and diluted in a 1:3 ratio with Buffer B.

The diluted supernate was then applied onto a heparin sepharose column (5 × 10 cm, previously equilibrated with Buffer B containing 0.1 M KCl). The column was washed with two column volumes of 0.1 M KCl in Buffer B to remove any unbound contaminants. The immobilized Srf I was then eluted using a 0.1 to 0.8 M KCl gradient in Buffer B. Fractions containing assayable restriction endonuclease activity as determined in Example 1b were collected, pooled and dialyzed against Buffer C (10 mM Tris-HCl at pH 8.0, 10 mM beta-mercaptoethanol, 5 mM EDTA, 1% Glycerol, 0.1% Triton X-100, 10 mM ammonium sulfate and 190 mM KCl).

After dialysis and titration, the partially purified restriction endonuclease Srf I was applied onto a Blue sepharose column (25 × 15 cm) (Pharmacia) previously equilibrated with Buffer C. The column was washed with two column volumes of Buffer C to remove any unbound contaminants and then the immobilized restriction endonuclease was eluted with a KCl gradient (0.19 M to 1.5 M). Fractions were collected into tubes preloaded with 50 μg/ml BSA and assayed for restriction enzyme activity as described in Example 1b. The fractions were also assayed for the presence of exonucleases and DNA binding proteins following methods familiar to one skilled in the art.

Fractions containing Srf I endonucleolytic activity were pooled and dialyzed against Buffer B containing 0.1 M KCl. After centrifuging the light precipitate at 12,000 rpm for 20 minutes in a JA14 rotor, the resultant supernate was applied to a heparin sepharose column (1.5×10 cm), previously equilibrated with Buffer B made in 0.1 M KCl. The column was washed with 2 column volumes of equilibration buffer to remove any unbound contaminants and Srf I was then eluted using a 0.1 to 0.8 M KCl gradient. Eluted fractions were collected into tubes preloaded with 100 µg/ml BSA. Endonuclease and exonuclease assays were performed on these column fractions and the endonuclease component was isolated from 90% of the exonuclease activity.

The resultant pooled partially purified I5 restriction endonuclease was then dialyzed against Buffer D (20 mM $KPO_4$, pH 7.0, 10 mM beta-mercaptoethanol, 5 mM EDTA, 40 mM KCl, 10 mM ammonium sulfate, 5% glycerol, 0.1% Triton X-100) and applied onto a Mono S (strong cationic exchanger based on monodisperse hydrophilic polymer particles, Pharmacia) FPLC column. Following a two column volume wash, the endonuclease was eluted with a KCl gradient (0.04 to 0.5 M KCl) into collection vials containing 100 µg/ml BSA. Srf I eluted at approximately 0.25 M KCl, prior to a second restriction enzyme, designated Srf II, the activity of which was distinct from Srf I. The monospecific Srf I activity fraction, determined by performing the assays described above, (substantially pure Srf I) were pooled and dialyzed to Buffer E (10 mM Tris-HCl at pH 8.0, 10 mM beta-mercaptoethanol, 5 mM EDTA, 40 mM KCl, 10 mM ammonium sulfate, 5% glycerol, 0.1% Triton X-100).

The dialyzed endonuclease was subsequently loaded onto a Mono Q (strong anionic exchanger based on monodisperse hydrophilic polymer particles, Pharmacia) column and washed with two column volumes of Buffer E. The immobilized endonuclease was eluted with a KCl gradient (0 to 0.3 M). FPLC fractions eluted from the Mono Q columns were collected into vials containing 100 µg/ml BSA and assayed as described above.

After chromatography on the Mono Q column above, the fractions containing Srf I activity (substantially pure Srf I) were pooled and dialyzed into Buffer F containing 10 mM $KPO_4$ at pH 7.0, 10 mM beta-mercaptoethanol, 1 mM EDTA and 0.1 M NaCl. The dialyzed endonuclease was then applied onto a 1.5×5 centimeter phosphocellulose column (Catalog Number, 407200, cellulose phosphate P-11 cationic exchanger, Whatman Biosystems Limited, Maidstone, Kent, England) that was pre-equilibrated with Buffer F. The column was then washed with two column volumes of Buffer F. The washed and immobilized endonuclease was eluted with a continuous salt gradient in Buffer F beginning with no NaCl up to 1 M NaCl. The fractions were collected into vials containing 100 µg/ml BSA. Fractions were then assayed for Srf I activity as described above.

Fractions containing Srf I activity were assayed for contamination by other nucleases and DNA binding proteins. Srf I activity-containing fractions, free of these contaminants, were determined to have endonuclease activity of 450,000 units (u). One unit is defined as the amount of restriction endonuclease required to cleave 1 µg of Adenovirus-2 DNA in one hour at 37° C. in a 50 µl reaction in 1X Universal Buffer as prepared in Example 1b. Thus, from 600 grams of Streptomyces rf cell paste, 450,000 units of activity were purified. The Srf I activity-containing fractions were then pooled into long term storage buffer (300 mM KCl, 10 mM Tris-HCl at pH 7.5, 10 mM beta-mercaptoethanol, 1 mM EDTA, 0.1% Triton X-100, 50% glycerol, and 200 µg/ml BSA). The characterization of the resultant purified Srf I restriction endonuclease is described below.

2. Characterization of the Novel Srf I Restriction Endonuclease a. Determination of Molecular Weight of Srf I

The molecular weight of Srf I was determined by both gel filtration methodology and by non-reducing SDS-PAGE. For the molecular weight determination by gel filtration, a Superose 12 column (cross-linked agarose, Pharmacia) was used following manufacturer's instructions. Briefly, the column was first equilibrated with a solution containing 0.5 M potassium chloride, 10 mM Tris-HCl, at pH 8.0, and 1 M EDTA. The molecular weight of Srf I was determined relative to the three molecular weight standards of beta-galactosidase (MW=116,000, Catalog Number G-8511, Sigma), trypsin inhibitor (MW=29,000, Catalog Number T-9767, Sigma) and carbonic anhydrase (MW=20,000, Catalog Number C-2273, Sigma).

The void volume of the column ($V_0$) was first determined to be approximately 6.64 milliliters (mls) by loading the beta-galactosidase protein marker as it was excluded based on its size from the column. The protein peaks were detected by measuring the optical density of the collected fractions at a wavelength of 280 nanometers. The elution volumes for the other two molecular weight standards, trypsin inhibitor and carbonic anhydrase, and the FPLC purified Srf I restriction endonuclease prepared in Example 1c were then measured. Carbonic anhydrase and trypsin inhibitor eluted at the respective volumes of 11.93 and 13.99 mls. Srf I eluted at 10.6 mls.

The molecular weights of the protein standards were plotted on log-log paper on the Y-axis against the calculated elution volume ($V_e$) divided by the void volume ($V_e/V_o$) For example, for beta-galactosidase, the $V_e/V_o=6.64$ divided by $6.64=1$; similarly, for trypsin inhibitor, the $V_e/V_o=13.88$ divided by $6.64=2.09$). Using line of best fit, Srf I was thus found to be approximately 55 kd by this methodology.

A second approach using sodium dodecylsulfate polyacrylamide gel electrophoresis (SDS-PAGE) was performed to determine the accuracy of the molecular weight determination of Srf I. A 12% Tris-glycine SDS-PAGE gel was prepared according to manufacturer's instructions (Catalog Number EC6005, Novex, Encinitas, CA). FPLC purified Srf I restriction endonuclease prepared in Example 1c was electrophoresed under non-reducing conditions in 1X Laemmli running buffer (10X Laemmli running buffer was prepared by admixing 303 grams of Tris base, 1442 grams of glycine, and 100 grams of SDS to 10 liters of water and pH was adjusted to 8.3) and compared to the following molecular weight standards obtained from Bio-Rad (Richmond, CA—Catalog Number 161—0304): rabbit muscle phosphorylase b (MW=97,400); BSA (MW=66,200); hen egg white ovalbumin (MW=45,000); bovine carbonic anhydrase (MW=31,000); soybean trypsin inhibitor (MW=21,500); and hen egg white lysozyme (MW=14,400).

After electrophoresis, the gel was stained with Coomassie blue to reveal the migrated positions of the proteins in the gel. Under these conditions, Srf I ran slightly in front of (or faster than) BSA, but slower than hen egg white ovalbumin, and thus was determined to have a relative molecular weight of approximately 64 kd. Thus, the approximate molecular weight of FPLC purified Srf I restriction endonuclease was determined to be between 55 kd based on Superose 12 column gel filtration and 64 kd based on SDS-page.

b. Determination of Cleavage Site Specificity of Srf I

1) Endonuclease Assays

Figure 1:
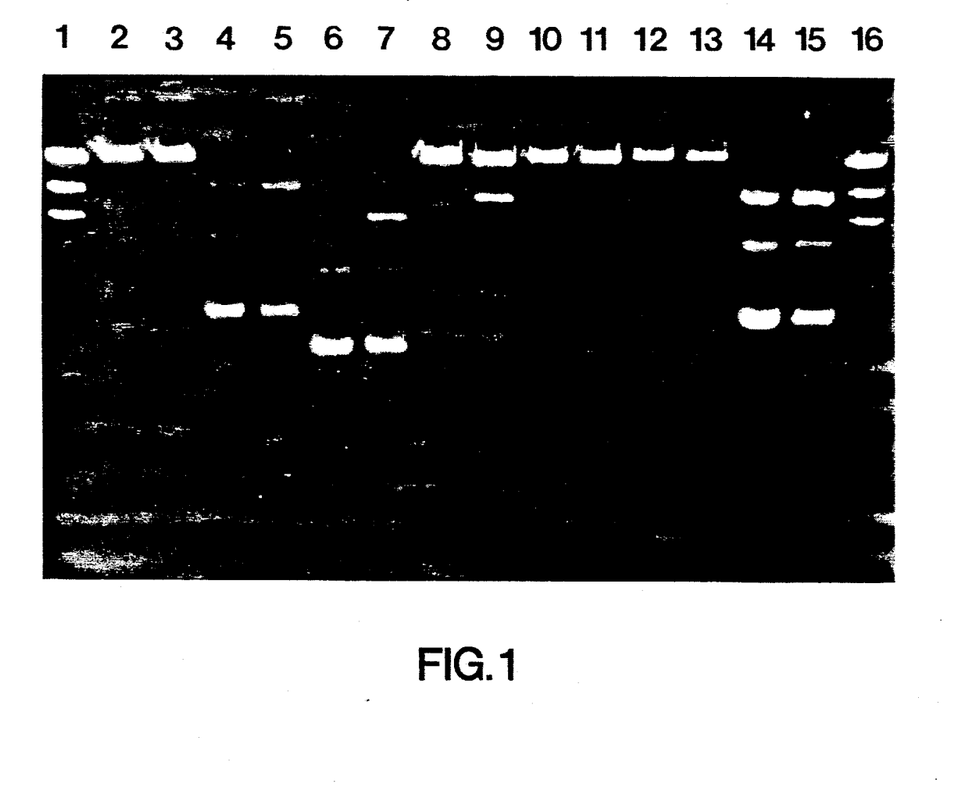
FIG. 1 illustrates the cleavage activity of Srf I on the DNA substrate Adenovirus-2 (Ad-2) which results in producing two fragments of 27,571 and 8,366 base pairs long as shown in Lane 9. Control undigested Adenovirus-2 is in Lane 8. Srf I failed to cleave the DNA templates, phage lambda (dam., dcm.), PhiX174, pBR322, T7, T5 and SV40. Each DNA substrate was electrophoresed on a 1% agarose gel in a pair-wise left and right arrangement to respectively compare undigested substrate to substrate maintained with Srf I. The lanes in FIG. 1 contain the following DNA: Lanes 1 and 16—Lambda Hind III molecular weight marker; Lanes 2 and 3—Lambda undigested + Srf 1 treated; Lanes 4 and 5—PhiX174 undigested and Srf I treated; lanes 6 and 7—pBR322 undigested and Srf I treated; Lanes 8 and 9—Adenovirus-2 undigested and Srf I treated; Lanes 10 and 11—T7 undigested and Srf I treated; Lanes 12 and 13—T5 undigested and Srf I treated; and Lanes 14 and 15—SV40 undigested and Srf treated.

Endonuclease assays were performed as described in Example 1b with FPLC purified Srf I restriction endonuclease on the following DNA substrates: Adenovirus-2, phage lambda (dam., dcm.), pBR322, PhiX174, T7, SV40 and T5. FIG. 1 shows the separate cleavage activity of Srf I on these DNA substrates. Srf I recognizes one site on Adenovirus-2 DNA producing two fragments of 27,571 and 8,366 base pairs long as shown in Lane 9 of FIG. 1. Srf I failed to cleave the remaining DNA substrates. These results suggested a rare, probable octanucleotide base pair recognition sequence. Preliminary mapping and double digestion of Adenovirus-2 DNA with Srf I and with Bam HI and Spe I localized the site to within 200 base pairs. A computer scan (Beckman Microgenie) for all novel eight base palindromes was performed.

Within the scanned nucleotide region, five possible palindromic recognition sequences were identified which were consistent with the rarity of Srf I cleavage. Of these possible sequences, three eight base pair recognitions sequences were found along with one ten base pair and one twelve base pair palindrome. The ten and twelve base pair palindromes were both extensions of one of the three eight base pair palindromic sequences. PCR amplification as described below was used to generate three Adenovirus2 DNA nucleotide sequence fragments, each containing one of the three palindromes of interest.

2) PCR of Octanucleotide Palindromes

PCR amplification of the three possible Srf I recognition sequences in Adenovirus-2 DNA was performed by first admixing 200 nanograms (ng) of Adenovirus-2 DNA with a PCR buffer consisting of 20 mM Tris-HCl at pH 8.8, 10 mM KCl, 6 mM $(NH_4)_2SO_4$, 1.5 mM $MgCl_2$ and 0.1% Triton X-100. To this admixture was admixed 0.25 mM each of dATP, dCTP, dGTP and dTTP (this corresponds to a 1/100 dilution of Stratagene's PCR grade dNTP mix, (Stratagene). Lastly, 250 ng in 1 μl of the selected synthetic oligonucleotides were admixed to form a PCR admixture. Eighty-two μl of distilled water was admixed to bring the PCR admixture to a final volume of 100 μl. The synthetic oligonucleotides used in the PCR reactions described below are shown in Table 1. The nucleotide sequence of each synthetic oligonucleotide having numerical designations from 873 to 878 is shown along with the corresponding SEQ ID NOs. The nucleotide bases of the regions of Adenovirus-2 to which the synthetic oligonucleotides correspond are also indicated in the table immediately below the 5' and 3' bases in each oligonucleotide. The polarity of each oligonucleotide is indicated as a "+" and a "−" for sense and anti-sense primers, respectively.

TABLE 1

| DESIGNATION ID | SEQ ID NO | POLARITY | NUCLEOTIDE SEQUENCE AND CORRESPONDING NUCLEOTIDE REGION OF ADENOVIRUS-2 DNA |
|---|---|---|---|
| 873 | 2 | − | 5'-CAGAGTTAGGATCGCCTGAC-3'<br>27727    27708 |
| 874 | 1 | + | 5'-GACGGGACATTTCAGATCGG-3'<br>27659    27678 |
| 875 | 3 | − | 5'-CTCCACTGGTCATTCAGTCG-3'<br>27911    27892 |
| 876 | 1 | + | 5'-CTCACCTGAAAATCAGAGGG-3'<br>27585    27604 |
| 877 | 4 | − | 5'-TCGTCGTTGAGCTGAATACC-3'<br>27627    27608 |
| 879 | 1 | + | 5'-CAGCGCCATTATGAGCAAGG-3'<br>27205    27224 |

Figure 4:
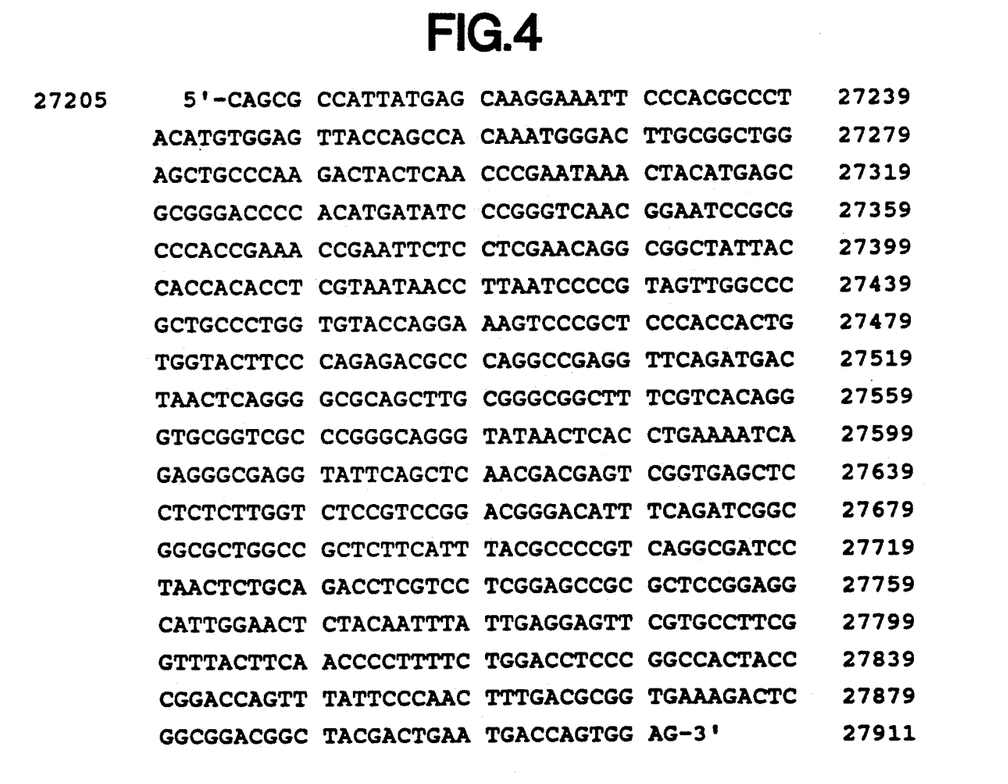
FIG. 4 illustrates the nucleotide sequence of a portion of the Adenovirus-2 gene beginning at nucleotide position 27205 and ending at 27911. The same sequence is also listed in the Sequence as SEQ ID NO 1 where the corresponding nucleotides are listed beginning at 1 and ending at 707.

To determine the Srf I cleavage site in Adenovirus-2 DNA, pairs of sense and anti-sense primers from Table 1 were admixed in three separate reactions to form three separate PCR fragments, A, B, and C, corresponding to a region of Adenovirus-2 DNA from nucleotide base number 27205 through 27911 shown in FIG. 4 and listed in Sequence Listing (SEQ ID NO 1).

To amplify fragment A, primers 874 and 875 were admixed. If Srf cleaved the resultant Fragment A between nucleotide base number 27727 and 27728, the resultant fragments would be 184 base pairs (bp) and 68 bp. To amplify fragment B, primers 873 and 876 were admixed. If Srf I cleaved the resultant Fragment B between nucleotide base numbers 27657 and 27658, the resultant fragments would be 70 bp and 72 bp. To amplify Fragment C, primers 877 and 878 were admixed. If Srf I cleaved the resultant Fragment C between nucleotide base numbers 27571 and 27572, the resultant fragments would be 366 bp and 56 bp.

The separate PCR admixtures described above were heated for 5 minutes at 100° C., then cooled for 5 minutes at 53° C. followed by centrifugation for 30 seconds. Three μl of *Pyrococcus furiosus* DNA Polymerase (Stratagene) were then admixed with each reaction admixture to initiate the amplification reaction. Thirty rounds of amplification were performed on a Perkin-Elmer Cetus Thermal Cycler, each round consisting of 75 seconds at 72° C., 75 seconds at 96° C., 60 seconds at 53° C. followed by ten minutes at 72° C. The amplified reaction products were then maintained overnight at 4° C. The resultant PCR products were then digested with Srf I and electrophoresed on a 10% native polyacrylamide gel.

Figure 2:
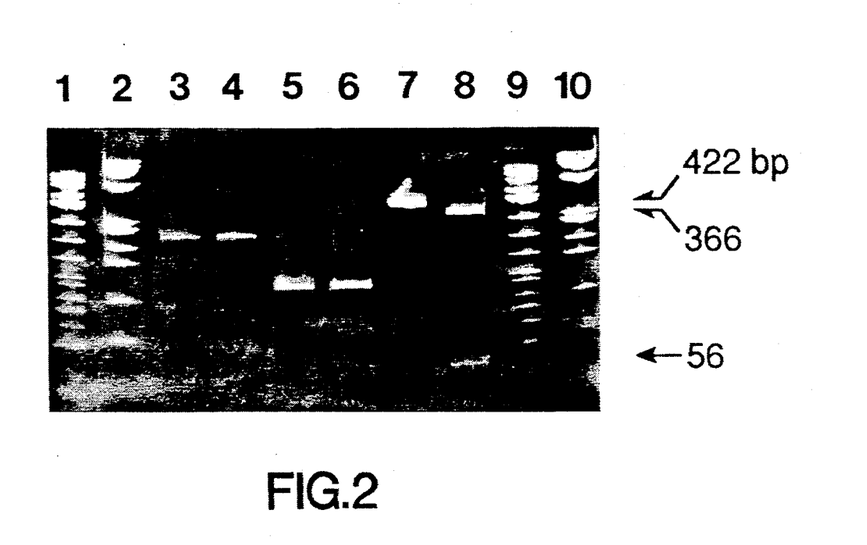

The results of the digestion of the palindromic octanucleotide PCR products are shown in FIG. 2, Lane 8, where cleavage occurred at nucleotide base number 27571 and the recognition sequence of Srf I was thus identified as the eight nucleotide base palindrome 5' GCCCGGGC 3' in fragment C having the nucleotide region from 27205 to 27627 of Adenovirus-2 DNA. Srf I cleaved the palindrome after the third C resulting in two fragments of 366 and 56 base pairs as shown in Lane 8. The fragments A and B were not digested by Srf I confirming the results seen with Fragment C.

3) Primed Synthesis Reaction

To confirm the cleavage site within the Srf I recognition sequence, the cleavage of a primed synthesis reaction was performed. pBluescript II SK+ (Stratagene), containing a recognition sequence for Srf I in its multi-cloning site, was used as a template. To accomplish this construction, a linker containing the Srf I recognition sequence determined above was cloned into the EcoR V site of the polylinker of pBluescript II SK+ (Stratagene) to form a plasmid template, pSMrrf I. One hundred nanograms (ng) of EcoR V-cleaved pBluescript II Sk+ were admixed with 50 ng of Srf I linker (double stranded 5'-CAAGCCCGGGCTTG-3'-SEQ ID NO 5) in 1X ligation buffer (50 mM Tris-HCl at pH 7.5, 7 mM MgCl$_2$, 1mM DTT and (1mM ATp) and 4 Weiss U T4 DNA ligase in a reaction volume of 25 µl. The ligation admixture was maintained for 16 hours at 15° C. Ligase was then inactivated by heating for 15 minutes at 72° C. The ligation reaction was then admixed with 6 U EcoR V and one-tenth volume of EcoR V cleavage buffer (10 mM DTT, Tris-HCl at pH 7.7, 150 mM NaCl, 10mM MgCl$_2$, 1 mM DTT and 100 µg/ml BSA) to form a reaction admixture. The admixture was then maintained for 30 minutes at 37° C. to form EcoRV cleavage products. EcoRV cleavage linearizes any wild-type pBluescript II Sk+ which ha self-ligated and does not contain the Srf I linker.

The EcoRV cleaved ligation was then used to transform E. coli strain SURE (Stratagene). Plasmid DNA was propagated overnight in SURE cells for cesium chloride gradient purification of the plasmid, pSMSrf I. The resultant template was first denatured and then Was admixed with T7 DNA polymerase, the M13 (−20) primer, previously end-labeled with $^{35}$S-ATP, and the four deoxynucleotides, dATP, dCTP, dGTP and dTTP. The reaction was maintained for five minutes at 37° C. to extend the primer beyond the nucleotide recognition site. The reaction product was subsequently cleaved with Srf I as prepared in Example 1c and then divided into four equal portions. Two of the resultant cleavage reactions were admixed with the four deoxynucleotides described above and maintained for ten minutes at 37° C. with 6 U Klenow fragment of DNA polymerase I to fill-in any overhang generated by restriction enzyme cleavage. One of the filled-in reactions and one of the control reactions were admixed with an equal volume of the standard sequencing "C" reaction and loaded next to the control reactions not mixed with C. Standard dideoxy sequencing reactions were carried out in parallel using T7 polymerase. All reaction mixtures were electrophoresed on a 8% denaturing polyacrylamide gel for DNA sequencing.

Figure 3:
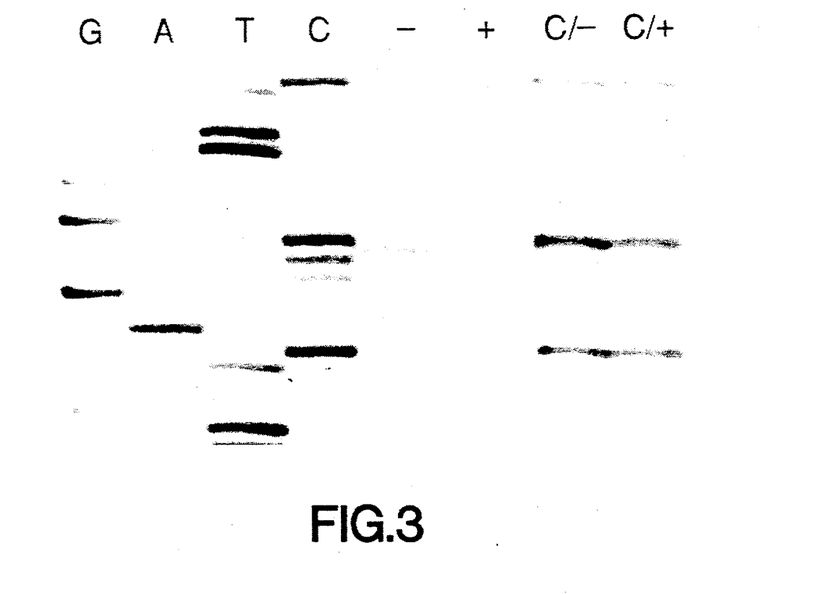

An autoradiograph of the primed synthesis reaction used to determine the cleavage site of Srf I is shown in FIG. 3. Lane 5 shows that the extended product was cleaved with Srf I producing a fragment which migrated between the second and the third C of the recognition sequence 5'-GCCCGGGC-3'. Because cleavage of the Fragment C produced by PCR in Example 2b2) above suggested cleavage after the third C, it was suspected that cleavage products were running slightly differently from the dideoxy sequencing reactions due to reaction buffer difference.

Mixing experiments described above confirmed this result. When cleavage reactions +/− Klenow fill-in were admixed with "C" sequencing reactions, the cleavage products ran with the third C in the sequence as shown in Lanes 7 and 8, respectively, of FIG. 3. That Srf I cleaved after the third C leaving blunt ends was demonstrated by the migration of the cleavage products +/− Klenow fill-in as shown in Lanes 5 and 6, respectively. No difference in migration was observed after Klenow fill-in of Srf I cleavage products. These results indicate that Srf I cleaved the DNA leaving blunt ends. The recognition sequence and cleavage site indicated by the asterisk are thus: 5' GCCC*GGGC- 3'.

The foregoing is intended as illustrative of the present invention but is not limiting. Numerous variations and modification can be effected without departing from the true spirit and scope of the invention.

---

What is claimed is:

1. An isolated restriction endonuclease Srf I having endonuclease specificity for, and a cleavage site in, a double stranded nucleotide sequence represented by the formula:

5' GCCC*GGGC 3'
3' CGGG*CCCG 5' wherein G and C respectively represent the nucleotides guanine and cytosine and * represents the Srf I cleavage site in each strand of said sequence.

2. The restriction endonuclease Srf I of claim 1 wherein said Srf I has a molecular weight of about 55 kd to about 64 kd.

3. The restriction endonuclease Srf I according to claim 1 wherein said Srf I is obtainable from a Streptomyces rf culture.

4. The restriction endonuclease Srf I according to claim 3 wherein said Streptomyces rf culture corresponds to that deposited under ATCC Accession Number 55215.

5. A method for producing a restriction endonuclease having endonuclease specificity for, and a cleavage site in, a double stranded nucleotide sequence represented by the formula:

5' GCCC*GGGC 3'
3' CGGG*CCCG 5' wherein G and C respectively represent the nucleotides guanine and cytosine and * represents the Srf I cleavage site in each strand of said sequence,
    which method comprises growing Streptomyces rf cells in a culture medium and recovering restriction endonuclease Srf I from the cultured cells.

6. The method of claim 5 wherein said Streptomyces rf culture corresponds to that deposited under ATCC Accession Number 55215.

7. The method of claim 5 wherein said Srf I has a molecular weight of about 55 kd to about 64 kd.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 707 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( x i ) SEQUENCE DESCRIPTION: SEQ ID NO:1:

```
CAGCGCCATT  ATGAGCAAGG  AAATTCCCAC  GCCCTACATG  TGGAGTTACC  AGCCACAAAT         60
```

```
GGGACTTGCG GCTGGAGCTG CCCAAGACTA CTCAACCCGA ATAAACTACA TGAGCGCGGG    120

ACCCCACATG ATATCCCGGG TCAACGGAAT CCGCGCCCAC CGAAACCGAA TTCTCCTCGA    180

ACAGGCGGCT ATTACCACCA CACCTCGTAA TAACCTTAAT CCCCGTAGTT GGCCCGCTGC    240

CCTGGTGTAC CAGGAAAGTC CCGCTCCAC CACTGTGGTA CTTCCCAGAG ACGCCCAGGC    300

CGAGGTTCAG ATGACTAACT CAGGGGCGCA GCTTGCGGGC GGCTTTCGTC ACAGGGTGCG    360

GTCGCCCGGG CAGGGTATAA CTCACCTGAA AATCAGAGGG CGAGGTATTC AGCTCAACGA    420

CGAGTCGGTG AGCTCCTCTC TTGGTCTCCG TCCGGACGGG ACATTTCAGA TCGGCGGCGC    480

TGGCCGCTCT TCATTTACGC CCCGTCAGGC GATCCTAACT CTGCAGACCT CGTCCTCGGA    540

GCCGCGCTCC GGAGGCATTG GAACTCTACA ATTTATTGAG GAGTTCGTGC CTTCGGTTTA    600

CTTCAACCCC TTTTCTGGAC CTCCCGGCCA CTACCCGGAC CAGTTTATTC CCAACTTTGA    660

CGCGGTGAAA GACTCGGCGG ACGGCTACGA CTGAATGACC AGTGGAG                 707
```

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( x i ) SEQUENCE DESCRIPTION: SEQ ID NO:2:

```
CAGAGTTAGG ATCGCCTGAC                                                 20
```

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( x i ) SEQUENCE DESCRIPTION: SEQ ID NO:3:

```
CTCCACTGGT CATTCAGTCG                                                 20
```

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( x i ) SEQUENCE DESCRIPTION: SEQ ID NO:4:

```
TCGTCGTTGA GCTGAATACC                                                 20
```

( 2 ) INFORMATION FOR SEQ ID NO:5:

(i) SEQUENCE CHARACTERISTICS:
    (A) LENGTH: 14 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

CAAGCCCGGG CTTG    14